US007595381B2

(12) United States Patent
Minekawa et al.

(10) Patent No.: US 7,595,381 B2
(45) Date of Patent: Sep. 29, 2009

(54) METHOD FOR DETECTING SARS CORONAVIRUS

(75) Inventors: Harumi Minekawa, Tochigi (JP); Keiko Watanabe, Tokyo (JP); Shinichi Kojiya, Tokyo (JP)

(73) Assignee: Eiken Kagaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/136,602

(22) Filed: Jun. 10, 2008

(65) Prior Publication Data
US 2009/0092962 A1 Apr. 9, 2009

Related U.S. Application Data

(62) Division of application No. 10/561,947, filed as application No. PCT/JP2004/008355 on Jun. 15, 2004, now Pat. No. 7,399,588.

(30) Foreign Application Priority Data

Jun. 27, 2003 (JP) ............................. 2003-184123
Nov. 14, 2003 (JP) ............................. 2003-384572

(51) Int. Cl.
*C07H 21/02* (2006.01)
(52) U.S. Cl. ...................................... 536/23.1; 435/975
(58) Field of Classification Search ........................ None
See application file for complete search history.

(56) References Cited

U.S. PATENT DOCUMENTS 5,474,796 A 12/1995 Brennan

FOREIGN PATENT DOCUMENTS

| CN | 1458281 A | 11/2003 |
|---|---|---|
| EP | 1020534 A1 | 7/2000 |
| EP | 1327679 A1 | 7/2003 |
| WO | 0028082 A1 | 5/2000 |
| WO | 0224902 A1 | 3/2002 |

OTHER PUBLICATIONS

The World Health Organization Update 49-SARS case fatality ratio, incubation period, May 7, 2003, Case fatality ratio (date of search: Jun. 24, 2003), URL: http://www.who.int/csr/sars/archive/2003_05_07/a/en.
"SARS: Diagnostic test methods", Apr. 29, Revision 4-1, date of search: Jun. 24, 2003, URL: http://idsc.nih.go.jp/others/urgent/update41-No.1html, the Infectious Disease Surveillance Center (IDSC), the National Institute of Infectious Diseases.
Drosten et al., "Identification of a Novel Coronavirus in Patients with Severe Acute Respiratory Syndrome", The New England Journal of Medicine, 2003, 348(20):1967-1976.
"SARS coronavirus gene detection using an RT-PCR method", date of renewal: May 16, 2003, date of search: Jun. 24, 2003, URL: http://idsc.nih.go.jp/others/urgent/update56-b.html, the Laboratory of Influenza Viruses, Department of Virology III, the Infectious Disease Surveillance Center (IDSC), the National Institute of Infectious Diseases.
Notomi et al., "Loop-mediated isothermal amplification of DNA", Nucleic Acids Research, 2000, 28(12):e63 (i-vii).
Yang et al., "Clinical Detection of polymerase gene of SARS-associated coronavirus", Journal of First Military Medical University, Department of Infectious Diseases, Nanfang Hospital, China, May 2003, 23(5):424-427.
Eiken Chemical Co., Ltd. "Eiken Kagaku, LAMP-ho o Riyo Shita SARS Corona Virus Kenshutsu Shiyaku Kaihatsu de Nagaski Daigaku Nettai Igaku Kenkyusho to Kyodo Kenkyu o Kaishi.", [online], Jun. 19, 2003, [retrieved on Aug. 3, 2004], retrieved from the Internet: <URL: http://www.tm.nagasaki-u.ac.jp/japanese/SARS_news_release.PDF>.
GenBank NC_004718.3, Jun. 23, 2003, M.A. Marra, et al., SARS coronavirus, complete genome, [retrieved on Aug. 3, 2004], Retrieved from the Internet: <URL: http://www.ncbi.nlm.nih.gov/entrez/viewer.fcgi?30271926:OLD12:897150>.
Fujitsu Ltd., "Press Release LAMP-ho no tameno Senyo Primer Sekkei Shien Service o Web de Teikyo LAMP-ho Seihin Hanbai no eMarket Place mo Unyo Kaishi.", [online], May 16, 2002, [retrieved on Aug. 3, 2004], Retrieved from the Internet: <URL: http://pr.fujitsu.com/jp/news/2002/05/16-1.html>.
Thai et al., "Development and Evaluation of a Novel Loop-Mediated Isothermal Amplification Method for Rapid Detection of Severe Acute Respiratory Syndrome Coronavirus", Journal of Clinical Microbiology, 2004, 42(5):1956-1961.
Zhou et al., "Identification and molecular cloning and sequence analysis of a novel coronavirus from patients with SARS by RT-PCR", Chinese J. Exp. Clin. Virol., 2003, 17(2):137-139.
Poon et al., "Rapid Detection of Severe Acute Respiratory Syndrome (SARS) Coronavirus by a Loop-Mediated Isothermal Amplification Assay", Clinical Chemistry, 2004, 50(6):1050-1052.
Teruo Kirikae, "Current Situation of SARS corona virus test methods and future prospects", Antibiotics & Chemotherapy, 2003, 20(1):63-69.
Poutanen et al., "Identification of Severe Acute Respiratory Syndrome in Canada", New England Journal of Medicine, 2003, 348(20):1995-2005.
Supplemental European Search Report dated Feb. 16, 2007.
Buck et al., "Design Strategies and Performance of Custom DNA Sequencing Primers", BioTechniques, 1999, 27(3):528-536.

*Primary Examiner*—Kenneth R. Horlick
*Assistant Examiner*—Christopher M. Babic
(74) *Attorney, Agent, or Firm*—Sughrue Mion, PLLC

(57) ABSTRACT

This invention provides: a method for detecting SARS pathogenic viruses with high sensitivity and rapidity for diagnosing severe acute respiratory syndrome (SARS); an oligonucleotide primer that can specifically hybridize with any nucleotide sequence constructed based on the nucleotide sequence of RNA polymerase of the SARS coronavirus; a method for nucleic acid amplification using such primer; a method for diagnosing infection with the SARS coronavirus via detection of nucleic acid amplification; and a kit for diagnosing SARS.

4 Claims, 4 Drawing Sheets

METHOD FOR DETECTING SARS CORONAVIRUS

This is a divisional of U.S. patent application Ser. No. 10/561,947 now U.S. Pat. No. 7,399,588 B2, filed Dec. 22, 2005, which is the National Stage of PCT/JP04/08355 filed Jun. 15, 2004, and which claims priority from Japanese Application No. 2003-184123 filed Jun. 27, 2003 and Japanese Application No. 2003-384572 filed Nov. 14, 2003. The entire disclosure of the prior application is hereby incorporated by reference.

TECHNICAL FIELD

The present invention relates to a method for detecting the severe acute respiratory syndrome (SARS) coronavirus and more particularly to a method for diagnosing SARS via a highly sensitive method for detecting genes.

BACKGROUND ART

Severe acute respiratory syndrome (hereinafter abbreviated as "SARS") is an infectious disease that began in Guandong, China in Nov. 2002, and has caused serious infection in nations such as Hong Kong, Taiwan, and Canada. According to the World Health Organization (WHO), the mortality for the patients afflicted with SARS is deduced to be 15% on average, and it is deduced to be 50% or higher in the case of patients aged 65 and over. The SARS coronavirus, which is a pathogenic virus of SARS, is a single-strand RNA virus (see, for example, non-patent document 1). It is known that this virus infects animals other than humans.

Major clinical symptoms of SARS are fever with temperatures of 38° C. or higher and respiratory problems, such as coughing and difficulty of breathing. In some cases, symptoms such as headache, shaking chills, loss of appetite, generalized malaise, diarrhea, or clouding of consciousness are observed. However, these symptoms are almost the same as those of other respiratory diseases, such as influenza. Thus, it is difficult to distinguish SARS from other diseases based solely on its symptoms.

An immunologic procedure has been known as a method of clinical testing. In such testing, the presence of an antibody against a viral antigen in blood, serum, urine, or saliva is inspected. The enzyme-linked immunosorbent assay (ELISA) and the immunofluorescence assay (IFA) are known techniques for detecting antibodies against the SARS coronavirus. With these techniques, however, antibodies cannot be detected at the early stage of the disease. In the case of ELISA, antibodies cannot be detected until 20 days after the development of the disease. In the case of IFA, antibodies cannot be detected until 10 days after the development of the disease (see, for example, non-patent document 2).

Also, a method for detecting antibodies via amplification of the virus gene via PCR has been known. This technique, however, has been problematic since it takes 1 hour or longer for amplification and detection, and the detection sensitivity thereof is low. Accordingly, a method for detecting the SARS coronavirus with rapidity and high sensitivity has been awaited (see, for example, non-patent documents 3 and 4).

The present inventors found that the aforementioned problems could be solved by the LAMP method, which is a method capable of detecting the SARS coronavirus with higher sensitivity and specificity within a shorter period of time compared with conventional techniques, such as immunoassay or PCR. Thus, the present inventors attained the object of the present invention.

[Non-Patent Document 1]

The World Health Organization Update 49-SARS case fatality ratio, incubation period, 7 May 2003, Case fatality ratio (date of search: Jun. 24, 2003),

[Non-Patent Document 2]

SARS: a method of diagnostic assay (April 29, Revision 4-1), date of search: Jun. 24, 2003, the Infectious Disease Surveillance Center (IDSC), the National Institute of Infectious Diseases

[non-patent document 3]

Drosten C., et al., New Eng. J. Med., 2003, vol. 348, pp. 1967-1976

[Non-Patent Document 4]

"Detection of SARS coronavirus gene via RT-PCR (date of renewal: May 16, 2003), date of search: Jun. 24, 2003, the Laboratory of Influenza Viruses, Department of Virology Iii, the Infectious Disease Surveillance Center (IDSC), the National Institute of Infectious Diseases

SUMMARY OF THE INVENTION

It is an object of the present invention to detect a pathogenic virus, i.e., the SARS coronavirus, with high sensitivity for early diagnosis of SARS.

The present inventors have conducted concentrated studies in order to attain the above object. As a result, they have found that the SARS coronavirus could be detected with high sensitivity by producing an oligonucleotide primer that can selectively hybridize with a SARS coronavirus-specific nucleotide sequence and amplifying a SARS coronavirus-specific nucleotide sequence by the LAMP method. This has led to the completion of the present invention.

Specifically, the present invention includes the following elements.

(1) An oligonucleotide primer designed based on any nucleotide sequence selected from nucleotides 41 to 256 of the nucleotide sequence of an RNA polymerase of the SARS coronavirus as shown in SEQ ID NO: 1 or a nucleotide sequence complementary thereto.

(2) The oligonucleotide primer according to (1) comprising at least 15 continuous nucleotides selected from the nucleotide sequences as shown in SEQ ID NOs: 2 to 13 selected from the nucleotide sequence of a RNA polymerase of the SARS coronavirus or a nucleotide sequence complementary thereto.

(3) The oligonucleotide primer according to (1) or (2) consisting of the nucleotide sequence selected from the following nucleotide sequences (a) to (d), provided that nucleotide sequence regions F3c, F2c, and F1c are selected from the 3'-terminus and nucleotide sequence regions R3, R1, and R1 are selected from the 5'-terminus of the target nucleic acid of the SARS coronavirus, and nucleotide sequences complementary thereto are determined to be F3, F2, and F1 and R3c, R2c, and R1c, respectively:

(a) a nucleotide sequence having the F2 region and the F1c region of the target nucleic acid at the 3'-terminus and the 5'-terminus, respectively;

(b) a nucleotide sequence having the F3 region of the target nucleic acid;

(c) a nucleotide sequence having the R2 region and the R1c region of the target nucleic acid at the 3'-terminus and the 5'-terminus, respectively; and (d) a nucleotide sequence having the R3 region of the target nucleic acid.

(4) The oligonucleotide primer according to any of (1) to (3) capable of amplifying a SARS coronavirus-specific nucleotide sequence and consisting of a nucleotide sequence selected from the following (e) to (h) from the 5'-terminus toward the 3'-terminus:

(e) 5'-(a nucleotide sequence complementary to the nucleotide sequence as shown in SEQ ID NO: 2)-(any nucleotide sequence comprising 0 to 50 nucleotides)-(the nucleotide sequence as shown in SEQ ID NO: 3)-3';

(f) 5'-(the nucleotide sequence as shown in SEQ ID NO: 5)-(any nucleotide sequence comprising 0 to 50 nucleotides)-(a nucleotide sequence complementary to the nucleotide sequence as shown in SEQ ID NO: 6)-3';

(g) 5'-(a nucleotide sequence complementary to the nucleotide sequence as shown in SEQ ID NO: 8)-(any nucleotide sequence comprising 0 to 50 nucleotides)-(the nucleotide sequence as shown in SEQ ID NO: 9)-3'; and (h) 5'-(the nucleotide sequence as shown in SEQ ID NO: 11)-(any nucleotide sequence comprising 0 to 50 nucleotides)-(a nucleotide sequence complementary to the nucleotide sequence as shown in SEQ ID NO: 12)-3'.

(5) A method for detecting the SARS coronavirus comprising amplifying a target nucleic acid region of the SARS coronavirus using the oligonucleotide primer according to any of (1) to (4).

(6) The method according to (5), wherein a target nucleic acid region of the SARS coronavirus is amplified by the LAMP method.

(7) A method for diagnosing severe acute respiratory syndrome (SARS) comprising diagnosing infection with the SARS coronavirus by detecting amplification of a target nucleic acid region of the SARS coronavirus using the oligonucleotide primer according to any of (1) to (4).

(8) A kit used for a method for diagnosing severe acute respiratory syndrome (SARS) comprising the oligonucleotide primer according to any of (1) to (4).

EFFECT OF THE INVENTION

According to the present invention, an oligonucleotide primer that can selectively hybridize with a SARS coronavirus-specific nucleotide sequence is produced, and a SARS coronavirus-specific nucleotide sequence is amplified by the LAMP method. Thus, the SARS coronavirus can be detected with high sensitivity and rapidity.

Hereafter, the present invention is described in detail.

Preferred Embodiments of the Invention

Samples that are used in the present invention are specimens obtained from humans or other animals suspected of having SARS. Examples thereof include sputum, bronchoalveolar lavage fluid, rhinorrhea, nasal aspirate, nasal wash, nasal sponge, pharyngeal sponge, mouth washing, saliva, blood, serum, blood plasma, spinal fluid, urine, stool, and tissue. In addition, specimens including, for example, cells used for infection experiments or the like, a culture solution thereof, or viruses separated from specimens obtained from organisms or cultured cells can be employed as samples. Such samples may be subjected to pretreatment such as separation, extraction, concentration, or purification.

Nucleic acids can be amplified by a novel technique of nucleic acid amplification that is referred to as the loop-mediated isothermal amplification (LAMP) method (WO 00/28082). This LAMP method was developed by Notomi et al. and eliminated the need for temperature control, which is indispensable for PCR. In this method, the 3' terminuses of template nucleotides are annealed, synthesis of complementary strands is started therefrom, and a primer that is annealed to the loop formed via the aforementioned synthesis is used in combination therewith. This enables nucleic acid amplification to be carried out under isothermal conditions. In the LAMP method, the 3' terminus of the primer is always annealed to a sample-derived region, and thus, a mechanism for checking upon complementary bonding of nucleotide sequences functions repeatedly. Consequently, nucleic acid amplification with high sensitivity and specificity is realized.

In the LAMP reaction, at least 4 types of oligonucleotide primers are used. These primers recognize a total of 6 regions in the nucleotide sequence of the template nucleic acid, i.e., the nucleotide sequences of F3c, F2c, and F1c regions from the 3' terminus and R3, R2, and R1 regions from the 5' terminus. These primers are referred to as inner primers F and R and outer primers F and R. The complementary sequences of F1c, F2c, and F3c are referred to as F1, F2, and F3, respectively, and the complementary sequences of R1, R2, and R3 are referred to as R1c, R2c, and R3c, respectively. An inner primer is an oligonucleotide that recognizes a "given nucleotide sequence region" on the target nucleotide sequence. It has on its 3' terminus the nucleotide sequence of the synthesis origin, and it has on its 5' terminus a nucleotide sequence complementary to any region of the product of nucleic acid synthesis originating from this primer. In the present invention, a primer comprising a "nucleotide sequence selected from F2" and a "nucleotide sequence selected from F1c" is referred to as an "inner primer F (hereafter abbreviated as "IPF")," and a primer comprising a "nucleotide sequence selected from R2" and a "nucleotide sequence selected from R1c" is referred to as an "inner primer R (hereafter abbreviated as "IPR")." In contrast, an outer primer is an oligonucleotide that recognizes "an arbitrary nucleotide sequence region located on the 3' terminal side of a 'given nucleotide sequence region'," and a nucleotide sequence serving as an origin of synthesis on the target nucleotide sequence. In the present invention, a primer comprising a "nucleotide sequence selected from F3" is referred to as an "outer primer F (hereafter abbreviated as "OPF")," and a primer comprising a "nucleotide sequence selected from R3" is referred to as an "outer primer R (hereafter abbreviated as "OPR")." "F" in each primer indicates a primer that complementarily binds to a sense strand of the target nucleotide sequence and functions as a synthesis origin. "R" indicates a primer that complementary binds to an antisense strand of the target nucleotide sequence and functions as a synthesis origin. The length of the oligonucleotide used as a primer is at least 10 nucleotides, and preferably at least 15 nucleotides. It may be chemically synthesized or naturally occurring. Each primer may be a single oligonucleotide or a mixture of a plurality of oligonucleotides.

In the LAMP method, another primer, i.e., a loop primer, can be used in addition to the inner and the outer primers. A loop primer has a nucleotide sequence that is complementary to a nucleotide sequence in a single-stranded region of the loop structure on the 5' terminal side of a dumbbell structure. With the use of such primer, the number of origins of nucleic acid synthesis can be increased, the reaction time can be shortened, and the detection sensitivity can be improved (WO 02/24902). The nucleotide sequence of the loop primer may be selected from the nucleotide sequence of the target gene or a complementary strand thereof. Alternatively, it may be another nucleotide sequence as long as it is complementary to the nucleotide sequence in the single-strand region in the loop structure on the 5' terminal side of the aforementioned dumbbell structure. A single type or two or mote types of loop primers may be used.

The SARS coronavirus is an RNA virus. When an RNA template is employed in the LAMP method, nucleic acid can be similarly amplified as with the case of a reaction using a DNA template by using a reaction solution prepared by adding a reverse transcriptase to the reaction solution for the latter type of reaction (the RT-LAMP method).

The present inventors have thoroughly studied the nucleotide sequences of primers for the LAMP method that can rapidly amplify a SARS coronavirus-specific nucleotide sequence and combinations thereof. As a result, they selected the following primer sets A and B based on the nucleotide sequence as shown in SEQ ID NO: 1 from the nucleotide sequence of an RNA polymerase of the SARS coronavirus (Drosten C., et al., New Eng. J. Med., 2003, vol. 348, pp. 1967-1976).

enzyme may be subjected to modification such as fragmentation or amino acid substitution.

After the LAMP reaction, a product of nucleic acid amplification can be detected via a conventional technique. For example, such product can be easily detected by using a labeling oligonucleotide that specifically recognizes an amplified nucleotide sequence or a fluorescent intercalator-based method (JP Patent Publication (Kokai) No. 2001-242169 A) or by subjecting the reaction solution after the completion of the reaction to agarose gel electrophoresis. The product of LAMP amplification is detected as a ladder of multiple bands of different nucleotide lengths via agarose gel electrophoresis. In the LAMP method, a large quantity of substrates are consumed upon nucleic acid synthesis, pyrophosphoric acid as a by-product is converted into magnesium pyrophosphate upon reaction with magnesium, which is also present therein, and the reaction solution becomes turbid to the extent such that such turbidity can be visually inspected.

```
(Primer set A)
IPF-A: 5'-TACATCAAAGCCAATCCACGCAATATGTTTATCACCCGCGAAGA-3'   (SEQ ID NO: 14)

OPF-A: 5'-ACCAAGTCAATGGTTACCCT-3'                           (SEQ ID NO: 4)

IPR-A: 5'-GCTGTCATGCAACTAGAGATGCTACAGCTACTAAGTTAACACCTG-3'  (SEQ ID NO: 15)

OPR-A: 5'-GTGTCAACATAACCAGTCGG-3'                           (SEQ ID NO: 16)

LPF-A: 5'-ACGAACGTGACGAATAGCT-3'                            (SEQ ID NO: 20)

LPR-A: 5'-GTACTAACCTACCTCTCCAGC-3'                          (SEQ ID NO: 21)

(Primer set B)
IPF-B: 5'-TGCATGACAGCCCTCGAAGAAGCTATTCGTCAC-3'              (SEQ ID NO: 17)

OPF-B: 5'-CTAATATGTTTATCACCCGC-3'                           (SEQ ID NO: 10)

IPR-B: 5'-GCTGTGGGTACTAACCTACCTGTCAACATAACCAGTCGG-3'        (SEQ ID NO: 18)

OPR-B: 5'-CTCTGGTGAATTCTGTGTT-3'                            (SEQ ID NO: 19)

LPF-B: 5'-AAAGCCAATCCACGC-3'                                (SEQ ID NO: 22)

LPR-B: 5'-CCAGCTAGGATTTTCTACAGG-3'                          (SEQ ID NO: 23)
```

Any template-dependent nucleic acid synthetases having strand displacement activity can be used for nucleic acid synthesis without particular limitation. Examples of such enzymes include Bst DNA polymerase (large fragment), Bca (exo-) DNA polymerase, and the Klenow fragment of *E. coli* DNA polymerase I. Bst DNA polymerase (large fragment) is preferable.

Any enzyme having activity of synthesizing DNA with the use of an RNA template can be used as a reverse transcriptase for the RT-LAMP method without particular limitation. Examples of such enzyme include reverse transcriptase, such as AMV, Cloned AMV, MMLV, SuperscriptII, ReverTraAce, and Thermoscript. Reverse transcriptase, such as AMV or Cloned AMV, is preferable. With the use of an enzyme having activity of reverse transcriptase and of DNA polymerase, such as Bca DNA polymerase, the RT-LAMP reaction can be carried out using a single enzyme.

An enzyme or reverse transcriptase that is used for nucleic acid synthesis may be purified from a virus or bacterium, or it may be prepared via gene recombination. Alternatively, such Accordingly, nucleic acid amplification can be detected with the elapse of time by observing such turbidity using a measuring apparatus that allows optical observation of the level of turbidity after the completion of a reaction or during a reaction, for example, measuring changes in absorbance at 400 nm using a general spectrophotometer (WO 01/83817).

Any of a variety of reagents that are necessary for detecting nucleic acid amplification with the use of the primer according to the present invention can serve as a pre-packaged kit. More specifically, the kit comprises various types of oligonucleotides that are necessary as primers according to the present invention or the loop primers, 4 types of dNTP that are substrates for nucleic acid synthesis, DNA polymerase for nucleic acid synthesis, an enzyme having activity of reverse transcriptase, a buffer or salts providing suitable conditions for enzyme reactions, a protecting agent for stabilizing enzymes or templates, and reagents necessary for detecting reaction products, according to need.

EXAMPLES

The present invention is hereafter described in greater detail with reference to the following examples, although the present invention is not limited thereto.

Example 1

Confirmation of Detection Sensitivity

Sensitivity of LAMP detection was compared with that of PCR detection.

1. Preparation of Samples and Reagents

1) Samples

RNA as shown in SEQ ID NO: 1 selected from RNA polymerase sequences of the SARS coronavirus was dissolved in a yeast RNA solution (50 ng/μl, Ambion), a dilution containing 10 to $10^4$ copies of RNA per μl and dilutions containing 2.5, 5, and 10 copies thereof were prepared, and these dilutions were designated as sample solutions. The aforementioned yeast RNA solution was designated as a sample solution containing 0 copies.

2) Composition and Concentration of Reagent Used for PCR

PCR was carried out in accordance with the method described in the non-patent document 4, wherein two types of primers each independently consisting of the nucleotide sequences as shown in SEQ ID NOs: 24 and 25 that amplify a 195-bp fragment of RNA polymerase were used as primers for detecting the SARS coronavirus.

Composition of cDNA Synthesis Reaction Solution
- 4 μL of 5× first strand buffer (Invitrogen)
- 1L of 10 mM dNTPs
- 2 L of 0.1M DTT
- 1 μL of random primer (50 ng/μl, TAKARA)
- 1 μL of RNase inhibitor (40 U/μl, Invitrogen)
- 1 μL of SuperScriptII (200 U/μl, Invitrogen)
- 5 μL of distilled water
- 5 μL of sample solution Composition of PCR Solution
- 5 μL of 10×Ex Taq buffer (Mg free) (TAKARA)
- 4 L of 25 mM $MgCl_2$
- 4 L of 2.5 mM dNTPs
- 1 μL each of 10 μmol/μL primer
- 0.5 μL of Ex Taq (5 U/μL, TAKARA)
- 33.5 μL of distilled water
- 1 μL of cDNA synthesis solution 3) Composition and Concentration of Reagent for the LAMP Method The concentrations of reagents in 25 μl of the final reaction solution were adjusted to the following levels for LAMP amplification with the use of the primer set A.

Composition of Reaction Solution
- 20 mM Tris-HCl (pH 8.8)
- 10 mM KCl
- 8 mM $MgSO_4$
- 1.4 mM dNTPs
- 10 mM $(NH_4)_2SO_4$
- 0.8 M Betaine (Sigma)
- 0.1% Tween 20
- 1.6 μM IPF and IPR
- 0.2 μM OPF and OPR
- 0.8 M LPF and LPR
- 0.625 U of AMV reverse transcriptase (Invitrogen)
- 8 U of Bst DNA polymerase (New England Biolabs)
- 0.25 μg/mL EtBr (Nippon Gene Co., Ltd.)

In the case of a reaction where the primer set B was used, 2 U of Cloned AMV reverse transcriptase (Invitrogen) was used instead of 0.625 U of AMV reverse transcriptase.

2. Reaction Via Nucleic Acid Amplification

1) Reaction Via PCR

A sample solution (5 μl) containing 0 or 10 to $10^3$ copies of the target sequences was added to the aforementioned cDNA synthesis solution, and the resulting mixture was subjected to cDNA synthesis at 42° C. for 50 minutes and then at 70° C. for 15 minutes. A solution of synthesized cDNA (1 μl) was added to the aforementioned PCR solution to bring the final amount thereof to 50 μl, and the reaction solution was subjected to PCR in a 0.2-ml dedicated purpose tube using a PTC-200 thermal cycler (MJ Research). A cycle of denaturation at 95° C. for 30 seconds, annealing at 56° C. for 30 seconds, and polymerase elongation at 72° C. for 30 seconds was repeated 40 times. The time required for completing PCR was approximately 1 hour. After the completion of the reaction, 5 μl of the reaction solution was subjected to 2% agarose gel electrophoresis.

2) Reaction Via LAMP

A sample solution (1 μl) containing 0 or 10 to $10^3$ copies of the target sequences was added to a reagent for LAMP using the primer set A to bring the final amount thereof to 25 μl, and the reaction solution was subjected to LAMP in a 0.2-ml dedicated purpose tube at 63° C. for 60 minutes. After the completion of the reaction, 5 μl of the reaction solution was subjected to 2% agarose gel electrophoresis.

3. Result of Comparing Sensitivity for Detecting Each Nucleic Acid Amplification Product Via Electrophoresis FIG. 1 shows the results of observing the detection sensitivity of PCR by electrophoresis, and FIG. 2 shows the results of observing the detection sensitivity of LAMP using the primer set A by electrophoresis. As a result, amplification products were observed both in PCR and in LAMP. In the case of PCR, a 195-bp specific band was clearly observed in a dilution containing $10^2$ copies; however, the amplification product was observed as an unclear band in the case of a dilution containing 10 copies. In contrast, a specific amplification product was observed as a ladder-like band in a dilution containing only 10 copies in the case of LAMP.

Example 2

Determination of Time Required for Real-time LAMP Detection

The time required for LAMP detection with the use of the primer set A was examined using 25 μl of the composition for the LAMP method in Example 1, using a real-time fluorescent measuring apparatus (PRISM 7700, Applied Biosystems), and fixing the reaction temperature at 63° C. The results are shown in FIG. 3.

As a result, no increase in fluorescence was observed in a sample containing 0 copies 60 minutes later. In contrast, an increase in fluorescence was observed in a sample containing 10 copies or more within 20 minutes. This indicates that 10 copies were detected within 20 minutes.

The time required for LAMP detection with the use of the primer set B was examined via real-time turbidimetry using a real-time turbidity measuring apparatus (LA-200, Teramecs Co., Ltd.). The LAMP reaction was carried out using the LAMP composition (25 µl) prepared in Example 1 and fixing the reaction temperature at 63° C. The results are shown in FIG. 4.

As a result, no increase in turbidity was observed in a sample containing 0 copies 60 minutes later. In contrast, an increase in turbidity was observed in a sample containing 2.5 copies or more within 35 minutes. This indicates that 2.5 copies were detected within 35 minutes.

SEQUENCE LISTING

Figure 1:
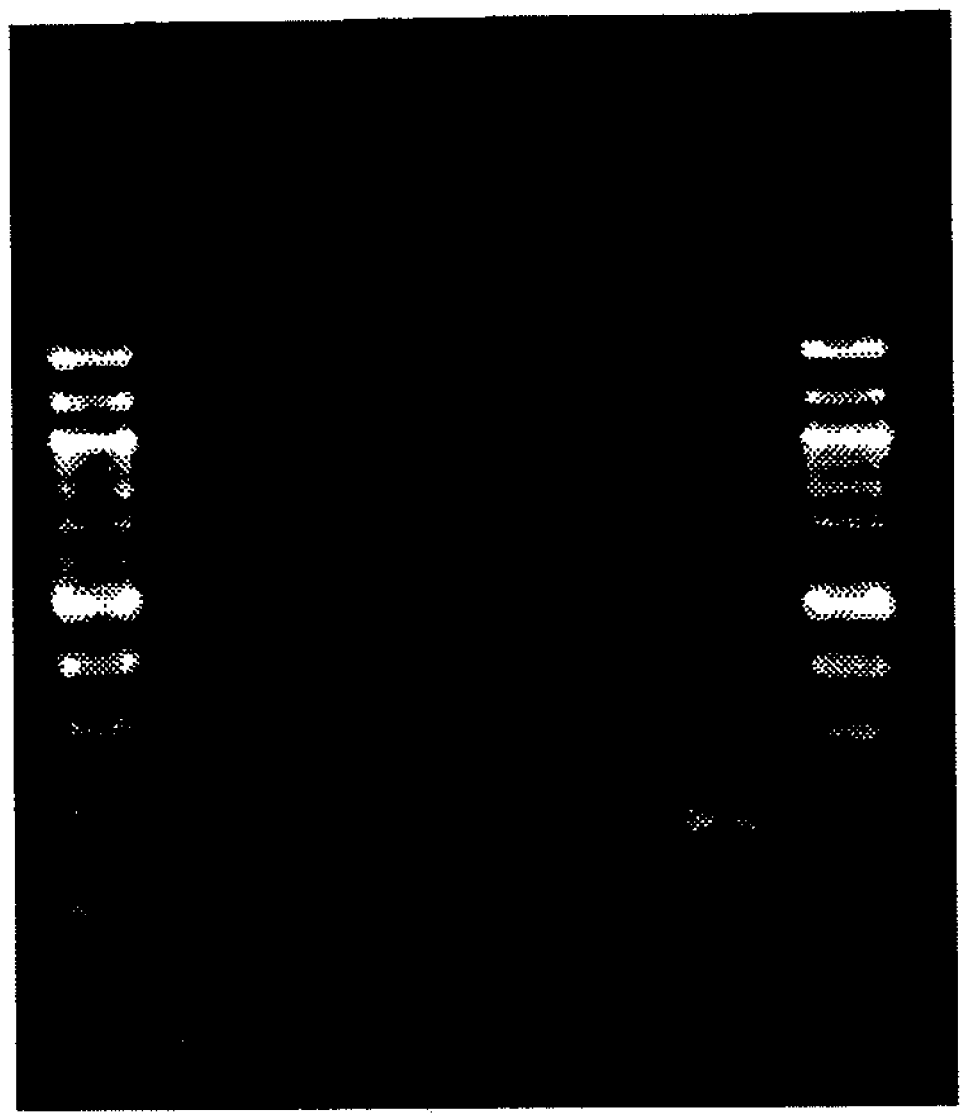
FIG. 1 shows sensitivity of PCR detection observed by electrophoresis (lanes 1 and 7: markers; lane 2: a reagent blank; lane 3: 0 copies; lane 4: 10 copies; lane 5: $10^2$ copies; and lane 6: $10^3$ copies).
Figure 2:
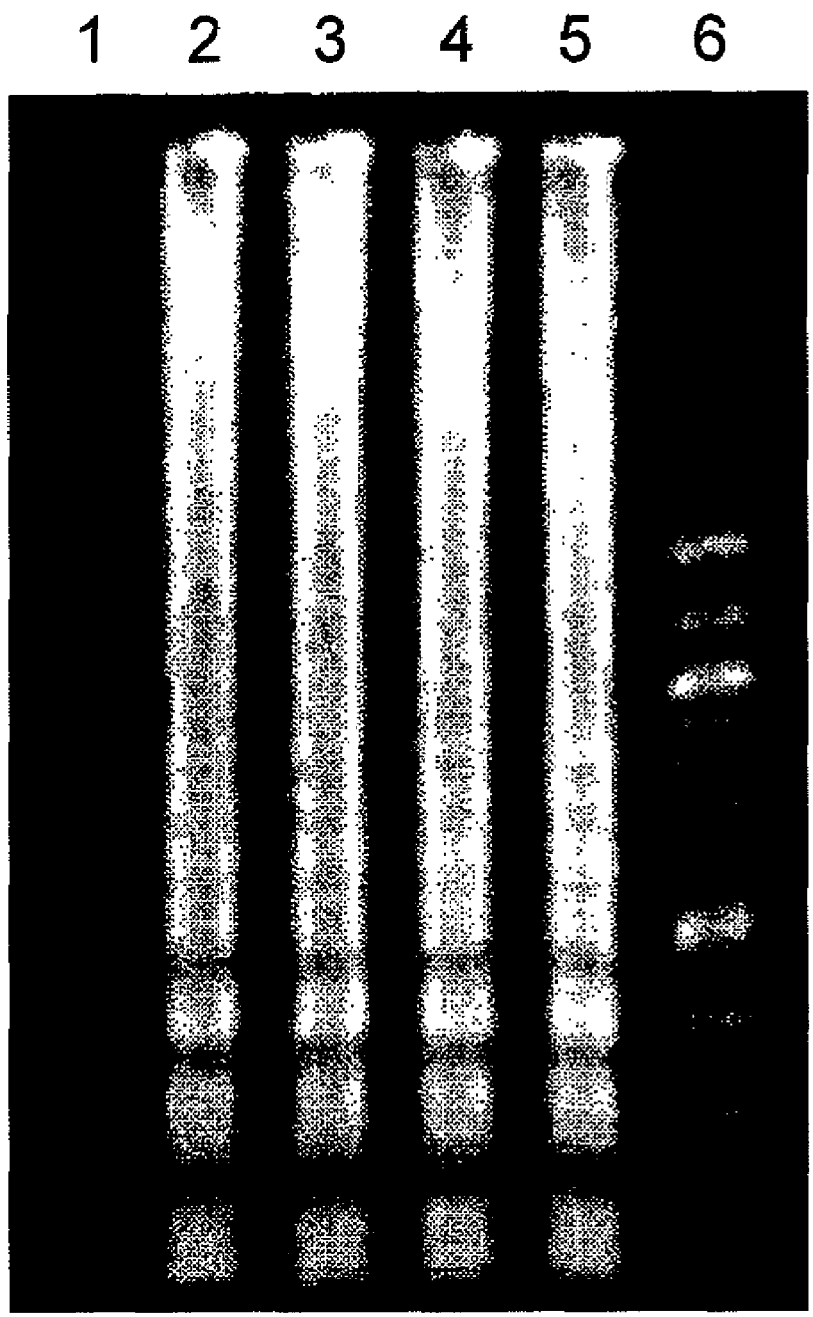
FIG. 2 shows sensitivity of LAMP detection using the primer set A observed by electrophoresis (lanes 1: 0 copies; lane 2: 10 copies; lane 3: $10^2$ copies; lane 4: $10^3$ copies; lane 5: $10^4$ copies; and lane 6: a marker).
Figure 3:
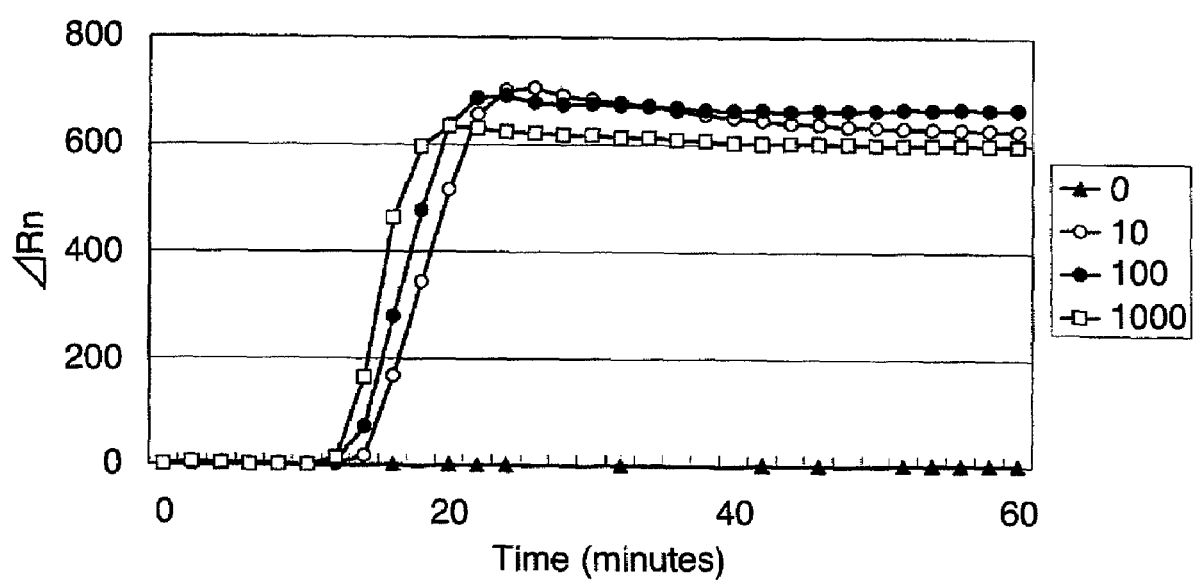
FIG. 3 shows the detection time of the real-time fluorescence assay using the primer set A.
Figure 4:
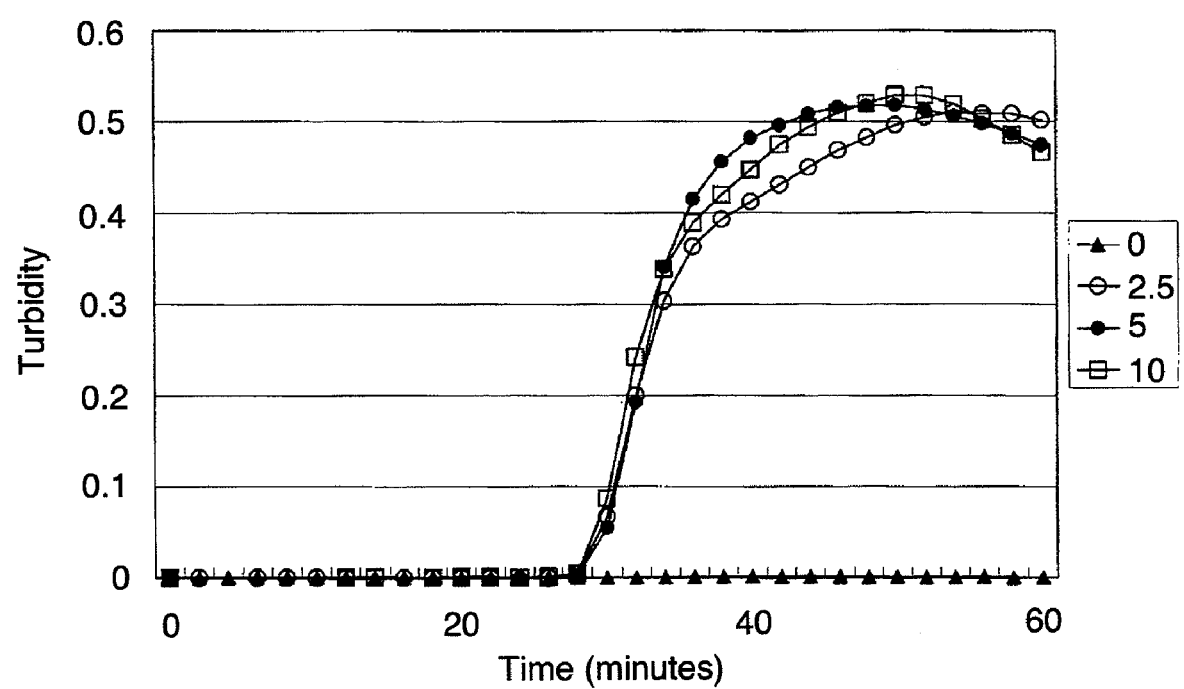
FIG. 4 shows the detection time of the real-time turbidimetry using the primer set B.

```
<160> NUMBER OF SEQ ID NOS: 25

<210> SEQ ID NO 1
<211> LENGTH: 300
<212> TYPE: RNA
<213> ORGANISM: SARS coronavirus

<400> SEQUENCE: 1
uaccguagac ucaucucuau gaugggguuuc aaaaugaauu accaagucaa ugguuacccu      60
aauauguuua ucacccgcga agaagcuauu cgucacguuc gugcguggau uggcuuugau     120
guagagggcu gucaugcaac uagagaugcu guggguacua acc

-continued accaagtcaa tggttaccct                    20

<210> SEQ ID NO 5
<211> LENGTH: 23
<212> TYPE: DNA
<213> ORGANISM: Artificial Sequence
<220> FEATURE:
<223> OTHER INFORMATION: Chemically synthesized oligonucleotide primer

<400> SEQUENCE: 5
gctgtcatgc aactagagat gct                    23

<210> SEQ ID NO 6
<211> LENGTH: 22
<212> TYPE: DNA
<213> ORGANISM: Artificial Sequence
<220> FEATURE:
<223> OTHER INFORMATION: Chemically synthesized oligonucleotide primer

<400> SEQUENCE: 6
caggtgttaa cttagtagct gt                    22

<210> SEQ ID NO 7
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 7
ccgactggtt atgttgacac                    20

<210> SEQ ID NO 8
<211> LENGTH: 15
<212> TYPE: DNA
<213> ORGANISM: Artificial Sequence
<220> FEATURE:
<223> OTHER INFORMATION: Chemically synthesized oligonucleotide primer

<400> SEQUENCE: 8
gagggctgtc atgca                    15

<210> SEQ ID NO 9
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 9
gaagaagcta ttcgtcac                    18

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 10
ctaatatgtt tatcacccgc                    20

<210> SEQ ID NO 11
<211> LENGTH: 21
<212> TYPE: DNA

-continued

```
<213> ORGANISM: Artificial Sequence
<220> FEATURE:
<223> OTHER INFORMATION: Chemically synthesized oligonucleotide primer

<400> SEQUENCE: 11
gctgtgggta ctaacctacc t                                              21

<210> SEQ ID NO 12
<211> LENGTH: 18
<212> TYPE: DNA
<213> ORGANISM: Artificial Sequence
<220> FEATURE:
<223> OTHER INFORMATION: Chemically synthesized oligonucleotide primer

<400> SEQUENCE: 12
ccgactggtt atgttgac                                                  18

<210> SEQ ID NO 13
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 13
aacacagaat tcaccagag                                                 19

<210> SEQ ID NO 14
<211> LENGTH: 44
<212> TYPE: DNA
<213> ORGANISM: Artificial Sequence
<220> FEATURE:
<223> OTHER INFORMATION: Chemically synthesized oligonucleotide primer

<400> SEQUENCE: 14
tacatcaaag ccaatccacg caatatgttt atcacccgcg aaga                     44

<210> SEQ ID NO 15
<211> LENGTH: 45
<212> TYPE: DNA
<213> ORGANISM: Artificial Sequence
<220> FEATURE:
<223> OTHER INFORMATION: Chemically synthesized oligonucleotide primer

<400> SEQUENCE: 15
gctgtcatgc aactagagat gctacagcta ctaagttaac acctg                    45

<210> SEQ ID NO 16
<211> LENGTH: 20
<212> TYPE: DNA
<213> ORGANISM: Artificial Sequence
<220> FEATURE:
<223> OTHER INFORMATION: Chemically synthesized oligonucleotide primer

<400> SEQUENCE: 16
gtgtcaacat aaccagtcgg                                                20

<210> SEQ ID NO 17
<211> LENGTH: 33
<212> TYPE: DNA
<213> ORGANISM: Artificial Sequence
<220> FEATURE:
<223> OTHER INFORMATION: Chemically synthesized oligonucleotide primer

<400> SEQUENCE: 17
tgcatgacag ccctcgaaga agctattcgt cac                                 33
```

<210> SEQ ID NO 18
<211> LENGTH: 39
<212> TYPE: DNA
<213> ORGANISM: Artificial Sequence:
<220> FEATURE:
<223> OTHER INFORMATION: Chemically synthesized oligonucleotide primer

<400> SEQUENCE: 18
gctgtgggta ctaacctacc tgtcaacata accagtcgg                            39

<210> SEQ ID NO 19
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 19
ctctggtgaa ttctgtgtt                                                  19

<210> SEQ ID NO 20
<211> LENGTH: 19
<212> TYPE: DNA
<213> ORGANISM: Artificial Sequence
<220> FEATURE:
<223> OTHER INFORMATION: Chemically synthesized oligonucleotide primer

<400> SEQUENCE: 20
acgaacgtga cgaatagct                                                  19

<210> SEQ ID NO 21
<211> LENGTH: 21
<212> TYPE: DNA
<213> ORGANISM: Artificial Sequence
<220> FEATURE:
<223> OTHER INFORMATION: Chemically synthesized oligonucleotide primer

<400> SEQUENCE: 21
gtactaacct acctctccag c                                               21

<210> SEQ ID NO 22
<211> LENGTH: 15
<212> TYPE: DNA
<213> ORGANISM: Artificial Sequence
<220> FEATURE:
<223> OTHER INFORMATION: Chemically synthesized oligonucleotide primer

<400> SEQUENCE: 22
aaagccaatc cacgc                                                      15

<210> SEQ ID NO 23
<211> LENGTH: 21
<212> TYPE: DNA
<213> ORGANISM: Artificial Sequence
<220> FEATURE:
<223> OTHER INFORMATION: Chemically synthesized oligonucleotide primer

<400> SEQUENCE: 23
ccagctagga ttttctacag g                                               21

<210> SEQ ID NO 24
<211> LENGTH: 24
<212> TYPE: DNA
<213> ORGANISM: Artificial Sequence
<220> FEATURE:

```
<223> OTHER INFORMATION: Chemically synthesized oligonucleotide primer

<400> SEQUENCE: 24
atgaattacc aagtcaatgg ttac                                          24

<210> SEQ ID NO 25
<211> LENGTH: 22
<212> TYPE: DNA
<213> ORGANISM: Artificial Sequence
<220> FEATURE:
<223> OTHER INFORMATION: Chemically synthesized oligonucleotide primer

<400> SEQUENCE: 25
cataaccagt cggtacagct ac                                            22
```

The invention claimed is:

1. A primer set for detecting SARS coronavirus comprising:
   a) a first oligonucleotide primer comprising SEQ ID NO: 17 or a nucleotide sequence entirely complementary to said first oligonucleotide primer,
   b) a second oligonucleotide primer comprising SEQ ID NO: 18 or a nucleotide sequence entirely complementary to said second oligonucleotide primer,
   c) a third oligonucleotide primer comprising at least 15 contiguous nucleotides of SEQ ID NO: 10 or a nucleotide sequence entirely complementary to said third oligonucleotide primer, and
   d) a fourth oligonucleotide primer comprising at least 15 contiguous nucleotides of SEQ ID NO: 19 or a nucleotide sequence entirely complementary to said fourth oligonucleotide primer.

2. The primer set of claim 1, further comprising
   a) a fifth oligonucleotide primer comprising at least 15 contiguous nucleotides of SEQ ID NO: 22, or a nucleotide sequence entirely complementary to said fifth oligonucleotide primer, and
   b) a sixth oligonucleotide primer comprising at least 15 contiguous nucleotides of SEQ ID NO: 23, or a nucleotide sequence entirely complementary to said sixth oligonucleotide primer.

3. A kit used for a method for detecting severe acute respiratory syndrome (SARS) comprising the primer set of claim 1.

4. The kit of claim 3, further comprising
   a) a fifth oligonucleotide primer comprising at least 15 contiguous nucleotides of SEQ ID NO: 22, or a nucleotide sequence entirely complementary to said fifth oligonucleotide primer, and
   b) a sixth oligonucleotide primer comprising at least 15 contiguous nucleotides of SEQ ID NO: 23, or a nucleotide sequence entirely complementary to said sixth oligonucleotide primer.

* * * * *